(12) United States Patent
Näslund

(10) Patent No.: US 9,579,160 B2
(45) Date of Patent: Feb. 28, 2017

(54) POSITIONING MARKER

(76) Inventor: Ingemar Näslund, Huddinge (SE)

( * ) Notice: Subject to any disclaimer, the term of this patent is extended or adjusted under 35 U.S.C. 154(b) by 45 days.

(21) Appl. No.: 14/116,573

(22) PCT Filed: May 8, 2012

(86) PCT No.: PCT/SE2012/050484
§ 371 (c)(1),
(2), (4) Date: Nov. 8, 2013

(87) PCT Pub. No.: WO2012/154116
PCT Pub. Date: Nov. 15, 2012

(65) Prior Publication Data
US 2014/0088419 A1 Mar. 27, 2014

(30) Foreign Application Priority Data
May 9, 2011 (SE) ...................................... 1150406

(51) Int. Cl.
*A61B 19/00* (2006.01)
(52) U.S. Cl.
CPC .............. *A61B 19/54* (2013.01); *A61B 90/39* (2016.02); *A61B 2090/3954* (2016.02); *A61B 2090/3966* (2016.02); *A61B 2090/3995* (2016.02)
(58) Field of Classification Search
CPC ............ A61B 19/54; A61B 2019/5495; A61B 2019/5466; A61B 2019/5454
See application file for complete search history.

(56) References Cited

U.S. PATENT DOCUMENTS 4,202,349 A * 5/1980 Jones ....................... A61B 6/12
128/899
2003/0208142 A1 11/2003 Boudewijn et al.
(Continued)

FOREIGN PATENT DOCUMENTS

CN 201790827 U 4/2011
EP 1 413 251 A1 4/2004
(Continued)

OTHER PUBLICATIONS

International Search Report for corresponding patent application No. PCT/SE2012/050484 dated Jul. 20, 2012.
(Continued)

*Primary Examiner* — Joseph M Santos Rodriguez
(74) *Attorney, Agent, or Firm* — Renner, Otto, Boisselle & Sklar, LLP

(57) ABSTRACT

The present invention relates to a positioning marker intended to be inserted in tissue. The marker is an elongated object with a longitudinal axis A and with a diameter perpendicular to said longitudinal axis, wherein the diameter is at the most 1.2 mm. The marker further has a predetermined total length $L_{TOT}$. The marker comprises a plurality of first segments 1 and a plurality of second segments 2, wherein the first and the second segments are arranged alternately after each others. The marker comprises a first material with a density of at least 10 g/cm³, and this material constitute at least 90% by volume of the marker, and a second material that is magnetic and that constitute at the most 10% by volume of the marker.

14 Claims, 1 Drawing Sheet

(56) References Cited

U.S. PATENT DOCUMENTS

| | | |
|---|---|---|
| 2004/0075048 A1 | 4/2004 | Zyromski |
| 2004/0092818 A1* | 5/2004 | Weaver et al. ............... 600/431 |
| 2005/0038355 A1 | 2/2005 | Gellman et al. |
| 2006/0201601 A1 | 9/2006 | Furst et al. |
| 2007/0238979 A1 | 10/2007 | Huynh et al. |
| 2008/0058769 A1 | 3/2008 | Naslund |
| 2008/0269601 A1* | 10/2008 | Schwamb .................... 600/426 |
| 2009/0131734 A1 | 5/2009 | Neustadter et al. |
| 2009/0221915 A1* | 9/2009 | Voegele ................ A61B 19/54 600/433 |
| 2009/0312633 A1 | 12/2009 | Widmark et al. |

FOREIGN PATENT DOCUMENTS

| | | |
|---|---|---|
| JP | 2004-513709 | 5/2004 |
| JP | 2007-528779 | 10/2007 |
| WO | 01/95794 A1 | 12/2001 |
| WO | 02/40077 | 5/2002 |
| WO | 2005018463 | 3/2005 |
| WO | 2005/089664 | 9/2005 |

OTHER PUBLICATIONS

Extended European Search Report for corresponding European Patent Application No. 12782438.1 dated Sep. 25, 2014.
English Translation of Office Action for corresponding Chinese Patent Application No. 201280022600.7 dated Jul. 9, 2015.

\* cited by examiner

POSITIONING MARKER

This application is a national phase of International Application No. PCT/SE2012/050484 filed May 8, 2012 and published in the English language.

TECHNICAL FIELD

The present invention relates to a positioning marker that is intended to be inserted in tissue according to the preamble of the independent claim.

BACKGROUND

When treating cancer tumors the doctor is preparing the treatment e.g. by planning how large the dose of the medicine shall be or how much the radiation therapy shall comprise. Basis for the planning of the radiation therapy is done e.g. by using computer tomography images. These images are nowadays more and more frequently combined with images from other media such as magnetic camera images (a magnetic camera is normally referred to as MRI=magnetic resonance imaging) and images from a PET camera (PET=Positron Emission Tomography) in order with more certainty to determine the tumor/-s extension in all directions.

In order to minimize the side effects on normal healthy tissue repeatedly radiation doses normally are given. At these times of treatment it is important to carefully reposition the body and the tumor area according to predetermined parameters so the tumor area not will be missed.

Electronic image giving plates have been used for many years in order to control the position of the skeleton when using high energetic therapy beams on 4-20 megavolts (MV), which normally are used. In recent years the beam accelerators that give rise to the radiation doses have been equipped with complementary equipment resulting in x-ray beams in the kilovolt area (kV). These beams in the kV area have properties differentiated from the high energetic MV beam. The beams in the kV area are decelerated not only by the mass coming in its way, but also by a decelerating force in relation to the density of the material that the beams are passing by and the decelerating force is increasing almost exponentially with higher density.

Positioning markers are used in order to show the location of a tumor in a human or an animal tissue. These markers are decelerating the x-ray beams so much that the marker becomes visible on monitors where the results from different media are shown. Gold has a high density of 19.3 g/cm$^3$, which makes it advantageously to be used as decelerating substance for the beams. Pure gold is also soft and possible to shape and is tolerated by the body since it is an inert material. The volume of gold may be limited so the substance becomes a thin wire, which also means that the marker may be inserted into the body be means of thin needles. Thereby the risk of bleedings and infections is minimized. Such a marker of gold is known by e.g. WO2006/004542 A1.

X-ray beams passing a body with a diameter of up until 60 cm give an image on the monitor by means of the beams having been decelerated to a varying extent in different parts of the tissue. If a small positioning marker of ca 0.25-1.2 mm in the tissue shall be able to influence the image the x-ray beams hitting on the marker must decelerate the x-ray beams to such extent that contrasting differences are giving in the image.

Markers that are put into tissue of human or animal will rest mainly in the same place the entire life. Thus, it is extremely important that the markers not cause mechanical damage or give rise to allergies or other state of ill-health. The marker must have sufficient size and have an appropriate density in order for the marker to be clearly depicted at MR examination.

The inventor has identified a need when using positioning markers of gold, which is related to the difficulty to make them visible on monitors from all media that are used in order to determine the extension of the tumor. In order to facilitate such that the images from the computer tomography and the magnetic camera may be superposed in the appropriate way it would be desirable that the positioning marker also is visible when using a magnetic camera. As an example small positioning markers of gold are not visible on magnetic camera images.

The purpose with the present invention is thus, to achieve a positioning marker that is visible on monitors for the majority of media being used in order to optimize the beam treatment planning. Further the marker shall satisfy the demands to be tolerated of the body and not to cause mechanical damage in the body of the person in which the marker is inserted.

SUMMARY

The object of the present invention is to address the problems outlined above.

These objects, and others, are achieved by the invention according to the appended independent claims.

Preferred embodiments are defined by the dependent claims.

According to a first aspect, the invention relates to a positioning marker intended to be inserted in tissue. The marker is an elongated object with a longitudinal axis and with a diameter of at the most 1.2 mm. The marker further has a predetermined total length. The marker comprises a plurality of first segments and a plurality of second segments, wherein the first and second segments are arranged alternately after each others. The marker comprises a first material with a density of at least 10 g/cm$^3$, and this material constitute at least 90% by volume of the marker, and a second material that is magnetic and that constitute at the most 10% by volume of the marker.

BRIEF DESCRIPTION OF THE DRAWINGS

The present invention will now be described in more detail, and with reference to the accompanying drawings, in which.

DETAILED DESCRIPTION

In the following description, the invention will be described in more detail with reference to certain embodiments and to the accompanying drawings. For purposes of explanation and not limitation, specific details are set forth, such as particular scenarios, techniques, etc., in order to provide a thorough understanding of the present invention. However, it is apparent to one skilled in the art that the present invention may be practised in other embodiments that depart from these specific details.

In order to make the marker visible on monitors when doing MR examination a magnetic material is required in or on the marker. The amount of such a material has to be adapted carefully in order to not make the marker move in the strong magnetic fields in the MR cameras. Patients with markers may be required to go through magnet camera examination many times during their lifetime.

Figure 1:
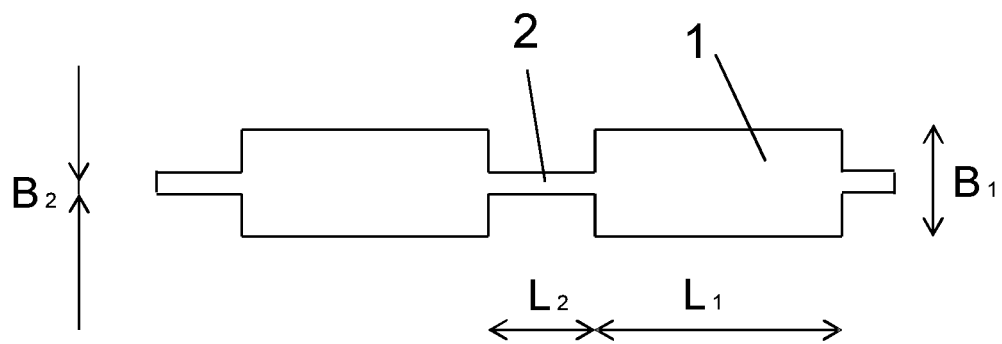
FIG. 1 shows a side view of a part of a positioning marker according to the invention.
Figure 2:
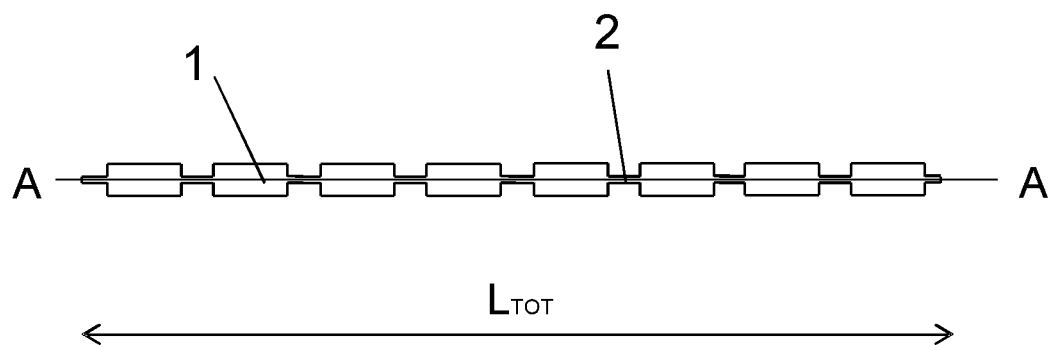
FIG. 2 shows a whole marker in elongated position.

FIG. 1 shows a side view of a part of a positioning marker according to the invention. A positioning marker contains a plurality of thicker parts, first segments 1 and a plurality of thinner parts, second segments 2 that are connecting two thicker parts with each other. A positioning marker has a total length of $L_{TOT}$ of about 10-30 mm, which may be seen in FIG. 2. The total length of the marker may also be shorter or longer. A preferred length is 20 mm. The relation of width between the first segments 1 and the second segments 2 is normally about 6:1. As an example the first segments 1 have a width $B_1$ that is between 0.15-0.3 mm and the second segments 2 have a width $B_2$ that is between 0.025-0.05 mm. In a preferred embodiment $B_1$ is 0.28 mm and $B_2$ 0.05. In another preferred embodiment $B_1$ is 0.20 mm and $B_2$ 0.03 mm. Further the first segments 1 e.g. have a length L that is about 2 mm and the second segments 2 e.g. a length $L_2$ that is about 1 mm.

The width of the first and second segments $B_1$ and $B_2$ may constitute a diameter, such that the first and second segments 1 and 2 have a circular cross section or an oval cross section. The segments may also be flat plates with the specified widths $B_1$ and $B_2$ arranged after each other's.

The positioning marker is intended to be inserted in tissue, and where the marker then is intended to be visible on images that are the result of different media. The marker is an elongated element with a diameter of at the most 1.2 mm and a predetermined total length $L_{TOT}$. The marker comprises a plurality of first segments 1 and a plurality of second segments 2, wherein the first and the second segments is arranged alternately after each other. The marker comprises a first material that has a density of at least 10 g/cm³, and this material constitute at least 90% by volume of the marker, and a second material that is magnetic and that constitute at the most 10% by volume of the marker.

The first material is preferably gold. And the second material is preferably iron. Preferably the content of the second material in the marker is 0.5% by volume of the markers volume. The content of the second material may also be smaller, such as slightly above 0, e.g. 0.01% by volume or 0.1 or 0.3% by volume. In further embodiments the content of the second material in the marker is 1; 2; 2.5; 5 or 7% by volume of the markers volume.

The predetermined total length $L_{TOT}$ of the marker is about 5 to 30 mm. Preferably, the total length of the marker is 20 mm.

The human body comprises iron to a small amount. An alloy or granulation mixture of up to 10% by volume iron in clean gold makes the marker visible when using an MR camera. The marker thus, needs to a larger part contain a substance or a material with high density in order to be visible in an x-ray. The marker's amount of iron that is exposed to tissue is negligible in relation to the daily recommended intake of iron per day for both children and adults. Also other ferromagnetic materials tolerated by the body such as magnetite, gadolinium, dysprosium or an alloy of different substances that constitute a ferromagnetic material may be used.

In an alternative embodiment of the invention a paramagnetic material is used instead of iron or a ferromagnetic material. Examples of paramagnetic materials are magnesium, molybdenum, lithium, and tantalum.

Iron or another ferromagnetic material or paramagnetic material is mixed or alloyed with gold. The amount of the ferromagnetic material in the marker thus, both has to be low in order to be tolerated by the body, but also be low in order not to cause the marker to move in the tissue due to the strong magnetic field in a magnetic camera.

When the marker is inserted in tissue suitably a hollow needle is used. In the part of the tissue where the tumor is located or has been located the marker will be pushed out of the needle and will be entangled to a solid ball of first and second segments. Preferably, the marker is pushed out of the needle by means of a so called mandrin. The inner diameter of the needle may be adapted to the larger diameter of the marker, i.e. the width $B_1$ of the first segments. The inner diameter of the needle may also be larger than the width $B_1$ in order to be able to arrange the marker folded in two or folded in three inside the needle. The inner diameter of the needle may be 0.44 mm when a marker with the width $B_1$ 0.20 mm is used, whereby the marker may be arranged folded in two. In order for the marker not to get stuck in the needle a lubricant that is compatible with the body may be used, e.g. special silicone approved for implant.

The percentage of the mixed iron in gold may vary around the given region, but not that much that the functional demands according to the above are disturbed. The mixture of iron and gold may also comprise other substances that are not pathogenic, e.g. radioactive substances for detection under surgical operation or PET camera examination.

What is mentioned above about gold may also be exchanged to other substances that have a high density and is tolerable by the body, e.g. platinum, silver or an alloy of appropriate materials that have a density of at least 10 g/cm³.

The marker is preferably manufactured by that a gold wire with an appropriate diameter, i.e. the diameter that constitutes the width $B_2$ of the second segments 2 is used. From this gold wire later on parts may be punched in order to create the first segments 1.

Further, the above mentioned and described embodiments are only given as examples and should not be limited to the present invention. Other solutions, uses, objectives, and functions within the scope of the invention as claimed in the accompanying patent claims should be apparent for the person skilled in the art.

The invention claimed is:

1. A positioning marker intended to be inserted in tissue via a needle, wherein the marker is an elongated object with a longitudinal axis (A) and with a diameter perpendicular to said longitudinal axis, wherein the diameter is at the most 1.2 mm, and wherein the marker has a predetermined total length ($L_{TOT}$), wherein the marker comprises a plurality of first segments having a first width ($B_1$), and a plurality of second segments having a second width ($B_2$), wherein the first width ($B_1$) is larger than the second width ($B_2$), and wherein the first and second segments are arranged alternately after each other along the longitudinal axis (A), wherein the marker comprises a first material with a density of at least 10 g/cm³, and this material constitutes at least 90% by volume of the marker, the marker comprises a second material that is magnetic and that constitute at the most 10% by volume of the marker, and the marker comprises an alloy or granulation mixture comprising the first material and the second material, and wherein the marker is configured to form an entangled ball of the first and second segments when inserted in tissue and existing the needle.

2. The positioning marker according to claim 1, wherein the first material is gold.

3. The positioning marker according to claim 1, wherein the second material is iron.

4. The positioning marker according to claim 1, wherein the content of the second material in the marker constitutes 0.5% by volume of the marker.

5. The positioning marker according to claim 1, wherein the predetermined total length ($L_{TOT}$) is between 5 and 30 mm.

6. The positioning marker according to claim 1, wherein the predetermined total length ($L_{TOT}$) is 20 mm.

7. The positioning marker according to claim 1, wherein the relation between the first width ($B_1$) and the second width ($B_2$) is 6:1.

8. The positioning marker according to claim 1, wherein the first width ($B_1$) is 0.3 mm and the second width ($B_2$) is 0.05 mm.

9. The positioning marker according to claim 1, wherein the first and second segments have a circular cross-section in a direction perpendicular to the longitudinal axis (A).

10. The positioning marker according to claim 1, wherein the first and second segments have an oval cross-section in a direction perpendicular to the longitudinal axis (A).

11. The positioning marker according to claim 1, wherein the first width ($B_1$) is 0.28 mm and the second width ($B_2$) is 0.05 mm.

12. The positioning marker according to claim 1, wherein the marker is configured to fold in two or in three.

13. A positioning marker intended to be inserted in tissue via a needle, wherein the marker is an elongated object with a longitudinal axis (A) and with a diameter perpendicular to said longitudinal axis, wherein the diameter is at the most 1.2 mm, and wherein the marker has a predetermined total length (LTOT), wherein the marker comprises a plurality of first segments having a first width (B1), and a plurality of second segments having a second width (B2), wherein the first width (B1) is larger than the second width (B2), and wherein the first and second segments are arranged alternately after each other along the longitudinal axis (A), wherein the marker comprises a first material with a density of at least 10 g/cm$^3$, and this material constitutes at least 90% by volume of the marker, the marker comprises a second material that is magnetic and that constitute at the most 10% by volume of the marker and in an amount sufficient to make the marker visible to an MR camera, and the marker comprises an alloy or granulation mixture comprising the first material and the second material, and wherein the marker is configured to form an entangled ball of the first and second segments when inserted in tissue and exiting the needle.

14. A positioning marker and needle assembly, comprising:

a needle;

a marker intended to be inserted in tissue, wherein the marker is an elongated object with a longitudinal axis (A) and with a diameter perpendicular to said longitudinal axis, wherein the diameter is at the most 1.2 mm, and wherein the marker has a predetermined total length (LTOT), wherein the marker comprises a plurality of first segments having a first width (B1), and a plurality of second segments having a second width (B2), wherein the first width (B1) is larger than the second width (B2), and wherein the first and second segments are arranged alternately after each other along the longitudinal axis (A), wherein the marker comprises a first material with a density of at least 10 g/cm$^3$, and this material constitutes at least 90% by volume of the marker, the marker comprises a second material that is magnetic and that constitute at the most 10% by volume of the marker, and the marker comprises an alloy or granulation mixture comprising the first material and the second material, wherein the marker is configured to form an entangled ball of the first and second segments when inserted in tissue and exiting the needle;

wherein the marker is arranged in a hollow of the needle and is configured to be pushed out from the hollow by a mandrin.

* * * * *